US011109868B2

(12) United States Patent
Forbes

(10) Patent No.: US 11,109,868 B2
(45) Date of Patent: Sep. 7, 2021

(54) LEFT ATRIAL APPENDAGE OCCLUDER DEVICE ANCHORING SYSTEM, ANCHOR, AND METHOD OF ATTACHMENT

(71) Applicant: Thomas J. Forbes, Grosse Pointe Park, MI (US)

(72) Inventor: Thomas J. Forbes, Grosse Pointe Park, MI (US)

(\*) Notice: Subject to any disclaimer, the term of this patent is extended or adjusted under 35 U.S.C. 154(b) by 168 days.

(21) Appl. No.: 16/177,605

(22) Filed: Nov. 1, 2018

(65) Prior Publication Data

US 2019/0069901 A1 Mar. 7, 2019

Related U.S. Application Data

(60) Division of application No. 15/292,975, filed on Oct. 13, 2016, now Pat. No. 10,143,478, which is a (Continued)

(51) Int. Cl.
*A61B 17/12* (2006.01)
*A61B 17/00* (2006.01)
*A61M 29/00* (2006.01)

(52) U.S. Cl.
CPC .... *A61B 17/12122* (2013.01); *A61B 17/0057* (2013.01); *A61B 17/1214* (2013.01);
(Continued)

(58) Field of Classification Search
CPC .......... A61B 17/0057; A61B 17/12022; A61B 17/12122; A61B 17/12172; A61B 12/12031; A61B 12/1204; A61B 17/1214; A61B 17/1219; A61B 17/12027; A61B 17/12168; A61B 2017/00575; A61B 2017/00606; A61B 2017/00615
See application file for complete search history.

(56) References Cited

U.S. PATENT DOCUMENTS 6,689,150 B1 2/2004 Van Tassel
7,303,526 B2 12/2007 Sharkey et al.
(Continued)

OTHER PUBLICATIONS

PCT/US2016/044005—International Preliminary Report on Patentability; International Search Report; and Written Opinion of the International Searching Authority.

*Primary Examiner* — Majid Jamialahmadi
(74) *Attorney, Agent, or Firm* — Luke C. Holst; McGrath North Mullin & Kratz, PC LLO

(57) ABSTRACT

The present invention relates in general to anchoring systems for occluder devices, and more specifically, to an anchoring system and method for implanting an occluder device within a left atrial appendage ("LAA") of the heart. The anchoring system is configured so that an anchor penetrates the inner endocardium layer, middle myocardium layer, and outer epicardium layer of an LAA wall. The purpose of the present invention is to provide an occluder device anchor that has a low risk of embolization and/or causing injury to neighboring valve structures. An additional purpose of the present invention is to provide an anchoring system and method for implanting an occluder device within the LAA that allows for the occluder device to be retrievable after initial placement, reusable, and repositionable for an optimal final placement within the LAA.

17 Claims, 13 Drawing Sheets

Related U.S. Application Data continuation-in-part of application No. 14/819,724, filed on Aug. 6, 2015, now abandoned, and a continuation-in-part of application No. PCT/US2016/044005, filed on Jul. 26, 2016, which is a continuation of application No. 14/819,724, filed on Aug. 6, 2015, now abandoned.

(52) U.S. Cl.
CPC .. *A61B 17/12031* (2013.01); *A61B 17/12172* (2013.01); *A61B 17/1219* (2013.01); *A61B 2017/00243* (2013.01); *A61B 2017/00349* (2013.01); *A61B 2017/00575* (2013.01); *A61B 2017/00592* (2013.01); *A61B 2017/00606* (2013.01); *A61B 2017/00615* (2013.01); *A61B 2017/00623* (2013.01); *A61B 2017/1205* (2013.01); *A61M 29/00* (2013.01)

(56) References Cited

U.S. PATENT DOCUMENTS

| | | |
|---|---|---|
| 7,597,704 B2 | 10/2009 | Frazier et al. |
| 2006/0212047 A1 | 9/2006 | Abbott et al. |
| 2006/0247672 A1 | 11/2006 | Vidlund et al. |
| 2008/0015635 A1 | 1/2008 | Olsen et al. |
| 2010/0211046 A1 | 8/2010 | Adams |
| 2011/0178539 A1 | 7/2011 | Homes, Jr. et al. |
| 2012/0065667 A1 | 3/2012 | Javois et al. |
| 2012/0283773 A1* | 11/2012 | Van Tassel ....... A61B 17/12022 606/213 |
| 2013/0317541 A1 | 11/2013 | Singhal et al. |
| 2014/0277074 A1 | 9/2014 | Kaplan et al. |
| 2015/0250482 A1* | 9/2015 | Slaughter ......... A61B 17/12036 606/200 |

\* cited by examiner

LEFT ATRIAL APPENDAGE OCCLUDER DEVICE ANCHORING SYSTEM, ANCHOR, AND METHOD OF ATTACHMENT

CROSS REFERENCE TO RELATED APPLICATIONS

This application is a divisional of U.S. patent application Ser. No. 15/292,975 filed Oct. 13, 2016, which is a continuation-in-part of U.S. patent application Ser. No. 14/819,72.4 filed Aug. 6, 2015 and PCT/US2016/044005 filed Jul. 26, 2016, herein incorporated by reference in their entirety.

FIELD OF THE INVENTION

The present invention relates in general to an anchoring system that would be able to be placed in the pericardial or extravascular space to anchor a medical device or occluder device within the heart itself. The present invention further includes a method of attaching and retrieving an occluder device in the left atrial appendage of the heart. The purpose of the invention is to provide an anchoring system and method of attaching and retrieving an occluder device that ensures optimal placement within the left atrial appendage of the heart. A further purpose of the present invention is to provide an anchor for an occluder device that has a low risk of embolization.

BACKGROUND OF THE INVENTION

Approximately 7 million Americans have what is known as non-valvular atrial fibrillation involving complications with the left atrial appendage of the heart (hereinafter, "LAA"). The LAA is a small, windsock shaped sac in the muscle wall of the left atrium. Though uncertain as to what function the LAA performs, if anything, what is certain is that in patients with non-valvular atrial fibrillation, 90% of the thrombus formation occurs in the body of the LAA. In normal conditions, electrical impulses that control a heartbeat travel in an orderly fashion throughout the heart. These electrical impulses cause the heart to contract wherein blood in the left atrium and LAA is driven into the left ventricle with each heartbeat. However, in patients with atrial fibrillation the electrical impulses are fast and chaotic, wherein many impulses begin at the same time and spread throughout the atria. For instance, a healthy atria contracts 60-80 times per minute, while a fibrillating atria quivers at 300-400 times per minute. Problems arise when the electrical impulses do not allow the atria enough time to fully contract and efficiently displace blood into the left ventricle from the left atrium and LAA. Consequently, blood pools and collects in the LAA due to inefficient contraction of the atria and the LAA's sac-like physiological structure, causing blood clots. Strokes may ultimately occur in patients when the blood clots are pumped out of the heart and embolize to the brain. Notably, individuals with atrial fibrillation are five to seven times more likely to have a stroke than the general population.

Treatment of atrial fibrillation typically involves oral anticoagulant therapy. Patient's taking blood thinners have noted a reduction in the risk of stroke by 65% as compared to patients without medication. The oral anticoagulant warfarin (COUMADIN®) has been traditionally utilized to minimize thrombus formation in patients with atrial fibrillation. Due to the requirement of frequent blood draws to monitor a patient's anticoagulation status, frequent interactions of the medication with either dietary changes or with other medications, and the high risk of encountering serious bleeding events, Coumadin has recently fallen into disfavor in the medical community. Newer medications including dabigatran (PRADAXA®) and rivaroxaban (XARELTO®) are also being utilized. The advantage of these newer medications are that they have less interaction with dietary changes and do not require blood draws to monitor a patient's anticoagulation status. However, these medications continue to encounter serious gastrointestinal bleeding events, are not reversible, and are extremely expensive.

Patients who cannot tolerate anticoagulants, or are not eligible for anticoagulant treatment due to pregnancy or other medical reasons, may elect to undertake various procedures to seal off or remove the LAA. One particular procedure, known as LAA occlusion, involves implanting a device into the heart that closes the LAA. Currently, there are several different occluder devices on the market or in current testing, including the WATCHMAN®, ATRICLIP®, PLAATO LAA Occlusion System®, AMPLATZER™, and the AMULET™. In each of these devices, the major technical difficulty encountered is to get the device to reliably fix itself within the LAA without embolizing or migrating out of the LAA into the systemic circulation. The reason for this is multifactorial, although primarily being related to the LAA coming in many different sizes and configurations. Some sizes and configurations of the are more amenable to device closure, whereas in others, device closure can be extremely difficult if not impossible to safely place an occluder device within the LAA.

The heart is comprised of three layers: (1) an inner endocardium layer; (2) a middle myocardium layer; and (3) an outer epicardium layer. The endocardium is a fragile, thin layer of tissue that lines the heart's chambers and valves. The myocardium is the thickest layer of the heart and is comprised of muscle tissue. The epicardium is a thin layer of visceral tissue. Between the heart and mediastinal space is the pericardium. The pericardium is a visceral layer of endothelium. The pericardial space lies in between the heart's epicardial surface and the pericardium. The pericardial space is filled with clear fluid that minimizes friction between the heart and other structures within the chest wall.

Current LAA occluder devices such as the WATCHMAN® and AMPLATZER™ have barbs on the outer edge of the device that latch on circumferentially to the endocardium layer of the LAA. Using barbs to fix the occluder device onto the endocardium layer of the LAA has significant disadvantages. For example, successfully "latching" an occluder device onto the endocardial layer of the LAA may be extremely difficult and time consuming for the interventional cardiologist. Problems are compounded if initial placement of the occluder device within the LAA is less than ideal, as the occluder device cannot be fully retrieved back within the delivery system without permanently damaging the retention barbs and/or the endocardium layer. Moreover, if the occluder device embolizes out of the LAA, irreparable damage to neighboring structures such as the mitral and/or aortic valves of the heart may occur in part, due to the presence of the barbs on the occluder device. Retrieval of an embolized occluder device is further complicated by the presence of the retention barbs.

Therefore, what is needed is an anchoring system and method for implanting an occluder device in the LAA that would allow for complete retraction and removal of the occluder device without permanently damaging the device. What is also needed is an anchoring system and method for implanting an occluder device in the LAA that provides a low risk of embolization and/or causing injury to neighboring valve structures. What is further needed is an anchoring system and method for implanting an occluder device that allows the occluder device to be positioned in multiple locations within the LAA, being able to be used in all types of LAA anatomy, and still result in optimal final placement of the occluder device within the LAA.

BRIEF SUMMARY OF THE INVENTION

Therefore, it is a principal object, feature, and/or advantage of the present invention to overcome the aforementioned deficiencies in the art and provide an anchoring system and method for implanting and retrieving an occluder device in the LAA.

A further object, feature, and/or advantage of the present invention is to provide an anchoring system and method for implanting and retrieving an occluder device in the LAA that may be used with a diverse range of LAA occluder devices.

Another object, feature, and/or advantage of the present invention is to provide an anchoring system and method for implanting and recapturing an occluder device in the LAA that minimizes the risk of the occluder device embolizing or migrating following release of the occluder device into the LAA.

Yet another object, feature, and/or advantage of the present invention is to provide an anchoring system and method for implanting an occluder device in the LAA that allows an interventional cardiologist to anchor the occluder device in multiple locations within the LAA.

A still further object, feature, and/or advantage of the present invention is to provide an anchoring system and method for implanting an occluder device in the LAA that allows the occluder device to be retrieved and adjusted within the LAA to achieve an optimal final position.

Another object, feature, and/or advantage of the present invention is to provide an anchoring system and method for implanting an occluder device in the LAA that causes minimal or no bleeding into the pericardial space upon anchoring.

A further object, feature, and/or advantage of the present invention is to provide an anchoring system and method for implanting an occluder device in the LAA that is easy to implant and retrieve by an interventional cardiologist.

A still further object, feature, and/or advantage of the present invention is to provide an anchoring system and method for implanting an occluder device in the LAA that allows the occluder device to be retrieved and adjusted by a interventional cardiologist within the LAA without damaging the occluder device.

These and/or other objects, features, and/or advantages of the present invention will be apparent to those skilled in the art. The present invention is not to be limited to or by these objects, features, and advantages. No single aspect need provide each and every object, feature, or advantage.

According to one aspect of the present invention, an anchoring system for implanting and retrieving an occluder device into a LAA comprises an outer sheath, a delivery catheter, an occluder device, and an anchor. The delivery catheter may be advanced through the outer sheath into the LAA, wherein the delivery catheter penetrates a wall of the LAA and enters the pericardial space creating a small hole. The anchor may comprise a first half and a second half connected by a shaft. The anchor may further comprise a contracted first position and a deployed second position. The occluder device, anchor catheter, and anchor may be advanced through the delivery catheter, wherein the anchor is in the contracted first position. The anchor catheter is further advanced to penetrate the LAA wall via the small hole and extend into the pericardial space. Specifically, the anchor catheter delivers the anchor, wherein the first half of the anchor remains inside the LAA and the shaft portion and the second half of the anchor penetrates the inner endocardium layer, middle myocardium layer, and outer epicardium layer of the LAA wall. Once inside the pericardial space, the second half of the anchor self-expands to the deployed second position within the pericardial space to implant the anchor in the LAA wall. The first half of the anchor remaining within the LAA also self-expands to the deployed second position, pinning the occluder device against the wall of the LAA. Alternatively, the anchor may be integral with the occluder device. The outer sheath releases the occluder device into the LAA, wherein it is held in position by the anchor. By mooring the occluder device through all three layers of the LAA wall via the anchor, the risk of embolization is reduced. Another aspect of the present invention includes a method of implanting and retrieving an occluder device into a LAA using the anchoring system described above.

Different aspects may meet different objects of the invention. Other objectives and advantages of this invention will be more apparent in the following detailed description taken in conjunction with the figures. The present invention is not to be limited by or to these objects, aspects, or figures.

BRIEF DESCRIPTION OF THE DRAWINGS

FIGS. 1-9 represent examples of the anchoring system, anchor, and method of the present invention.

FIG. 1 is a view of an outer sheath of one aspect of an anchoring system of the present invention and method for implanting and retrieving an occluder device within a LAA.

FIG. 2 is a view of an outer sheath, a delivery catheter, and an optional inner dilator of the anchoring system and method of FIG. 1, wherein the inner dilator and delivery catheter penetrate the LAA wall.

FIG. 8 is a view of the anchoring system and method of FIG. 2 if problems arise after deployment of the occluder device, wherein the occluder device is retracted inside the outer sheath and the first half of the anchor is retracted inside the anchor catheter.

FIG. 9 is a view of the anchoring system and method of FIG. 2 if problems arise after deployment of the occluder device, wherein the anchor is left implanted in the LAA wall.

DETAILED DESCRIPTION OF THE INVENTION

Figure 1:
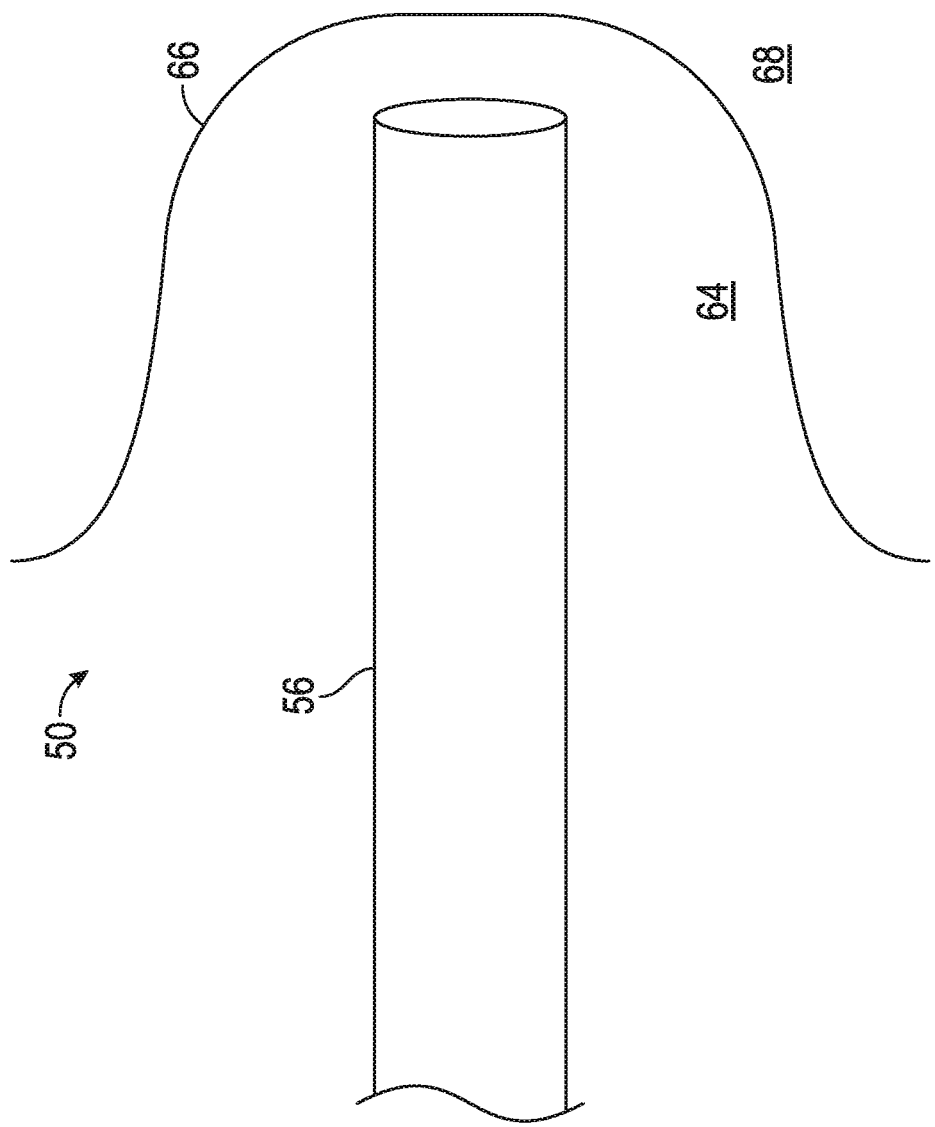

FIG. 1 illustrates one aspect of the present invention, an anchoring system 50 for implanting and retrieving an occluder device within a LAA. The anchoring system 50 may comprise an outer sheath 56. A balloon-occlusion catheter may also be utilized by the present invention. However, it is intended that other catheters standard in the industry may also be utilized. The outer sheath 56 may be inserted into LAA 64 via the left atrium proper of the heart by crossing the atrial septum using a transeptal procedure. If a balloon-occlusion catheter has been utilized, the balloon occlusion may be expanded to occlude the LAA 64 from the left atrium proper. Expanding the balloon occlusion may improve stabilization of the outer sheath 56 within the LAA 64 and allow for better imaging of the LAA 64 by an interventional cardiologist.

Figure 2:
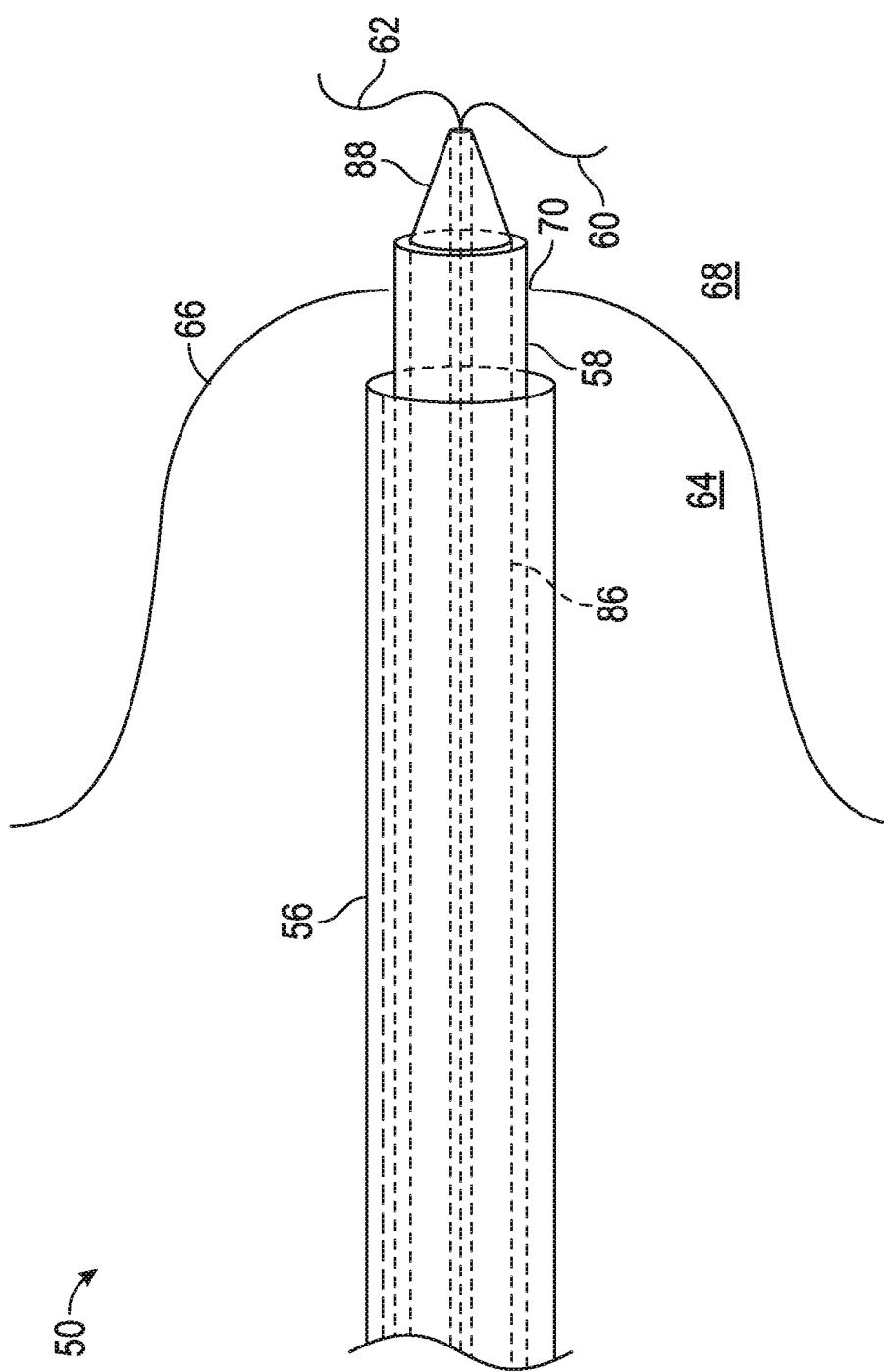

Illustrated in FIG. 2, the anchoring system 50 of the present invention further comprises a delivery catheter 58 and an optional inner dilator 86, wherein the inner dilator 86 includes a pointed distal end 88. The delivery catheter 58 and inner dilator 86 may be configured to encompass a delivery wire 60 and/or a buddy wire 62, wherein the delivery wire 60 and buddy wire 62 may traverse through an inner lumen of the delivery catheter 58 and inner dilator 86. The delivery wire 60 and/or buddy wire 62 may be of types standardly used in the industry, wherein a diameter of the delivery wire 60 may range between approximately 0.025-0.052 inches and a diameter of the buddy wire 62 may range between approximately 0.008-0.025 inches. The delivery catheter 58 and the inner dilator 86 may be advanced through the outer sheath 56 to the LAA wall 66. Using the pointed distal end 88 of the inner dilator 86, the inner dilator 86 and the delivery catheter 58 may be further advanced through the inner endocardium layer, middle myocardium layer, and outer epicardium layer to penetrate the LAA wall 66 and create a small hole 70. Thus, the pointed distal end 88 of the inner dilator 86, along with a distal end of the delivery catheter 58 and the delivery wire 60 and buddy wire 62, may extend into the pericardial space 68. When utilized, the inner dilator 86 may be subsequently removed from the delivery catheter 58, wherein the distal end of the delivery catheter 58 remains extending into the pericardial space 68. Alternatively, when the inner dilator 86 is not being utilized the delivery catheter 58 may be advanced through the inner endocardium layer, middle myocardium layer, and outer epicardium layer to penetrate the of the LAA wall 66 and create small hole 70.

Figure 3A:
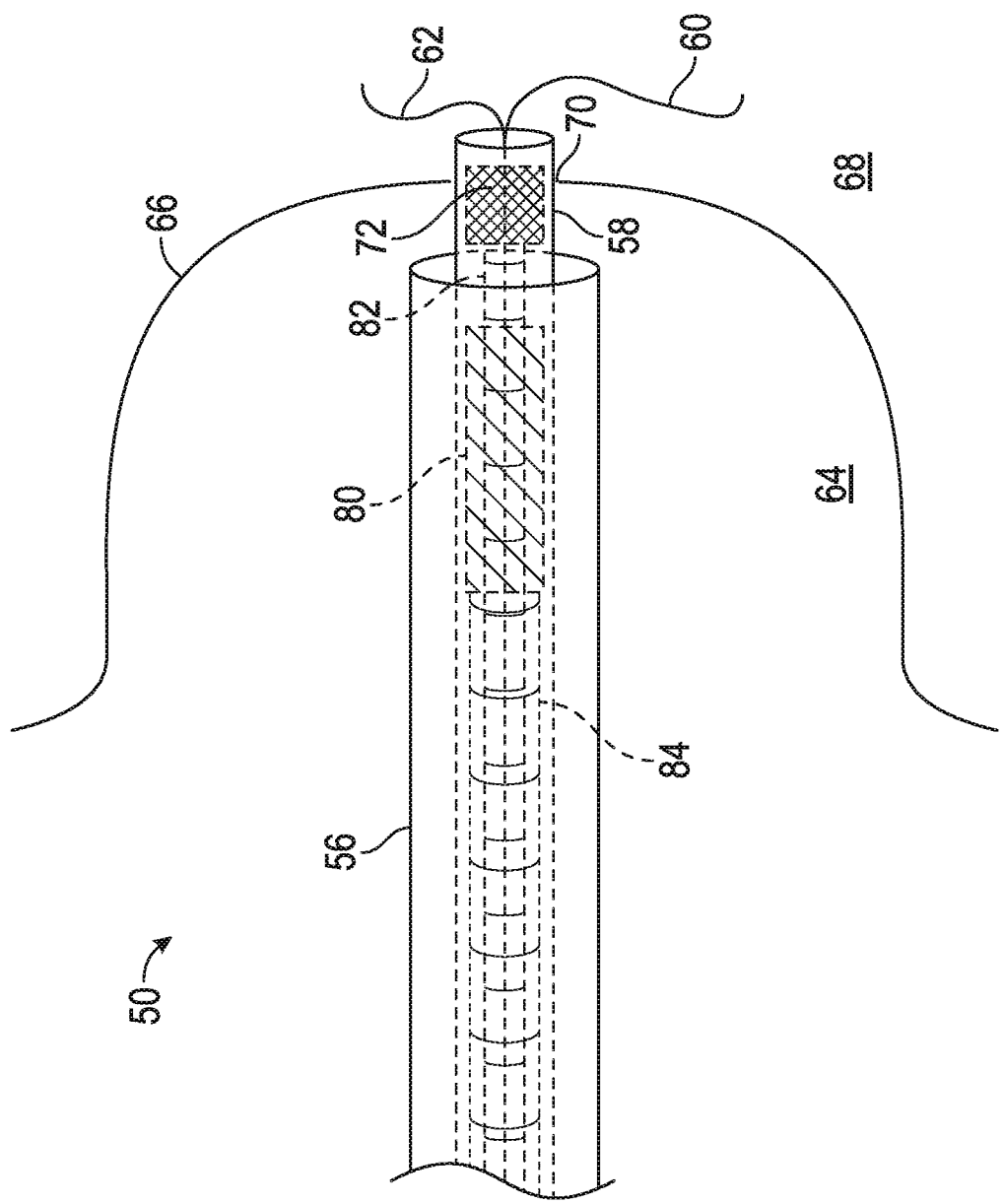
FIG. 3A is a view the anchoring system and method of FIG. 2, wherein an occluder device and an anchor are advanced through the outer sheath and anchor catheter, respectively.

Illustrated in FIG. 3A, the anchoring system 50 of the present invention further comprises an occluder device 80 and an occluder cable 84. It is contemplated that the anchoring system 50 of the present invention may be used with a diverse range of LAA occluder devices 80 such as coil implants, foam plugs, expandable frames, combinations thereof, and other occluder devices currently used in the industry and/or to be developed in the future. Specific examples of occluder devices 80 that may be used by the present invention include, but are not limited to, WATCHMAN®, ATRICLIP®, PLAATO LAA Occlusion System®, AMPLATZER™, and AMULET™. In the present invention, the occluder device 80 may have a distal end with a hole approximately 1-5 mm in diameter.

Figure 3B:
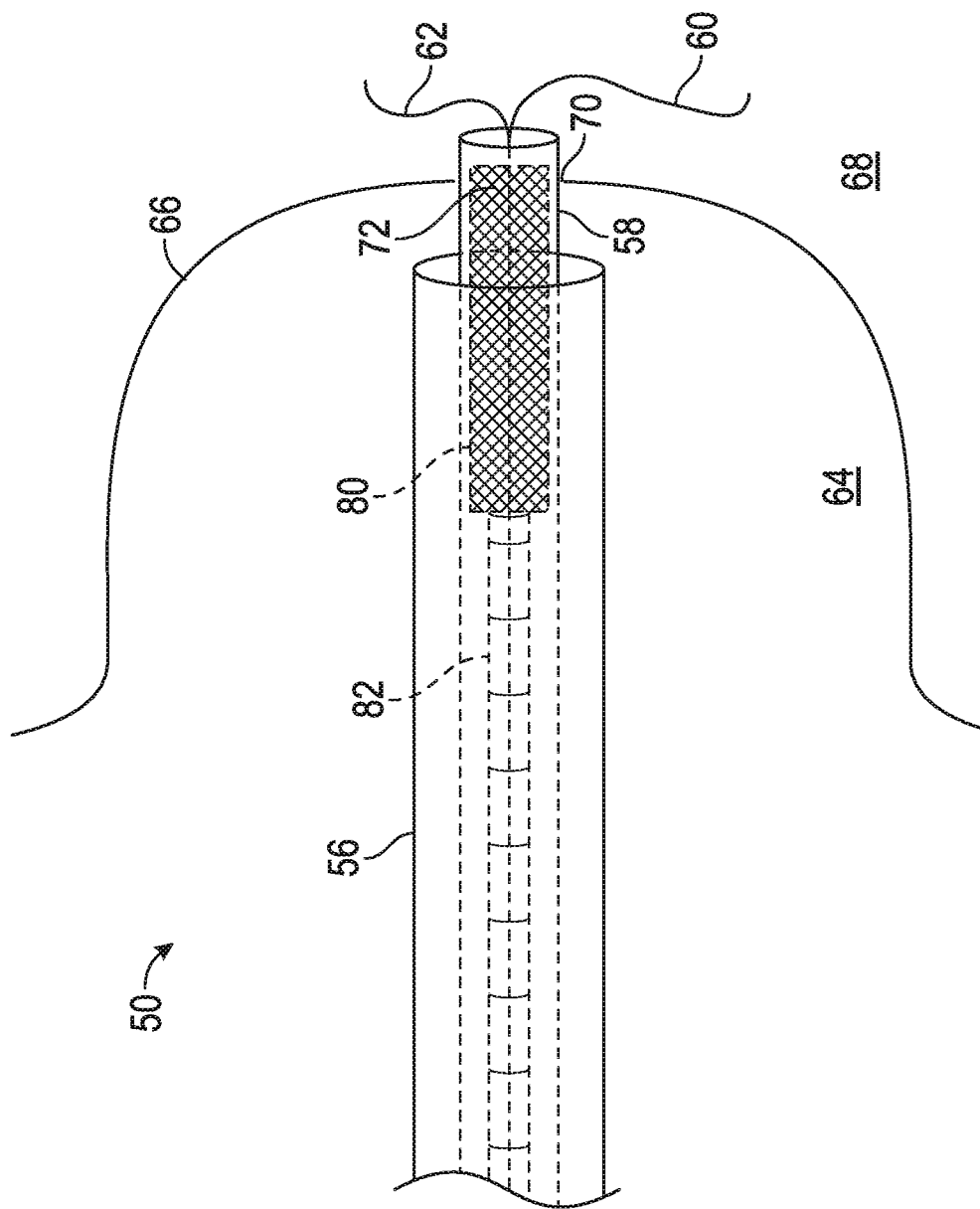
FIG. 3B is a view the anchoring system and method of FIG. 3A, wherein the occluder device and anchor are integral.

As shown in FIG. 3A, the occluder cable 84 may be a hollow coaxial cable standardly used in the industry. The occluder cable 84 may be attached to the occluder device 80, wherein the occluder cable 84 may be used for deploying and retrieving the occluder device 80 within the LAA 64. The occluder device 80 and the occluder cable 84 may reside inside the delivery catheter 58. The delivery catheter 58 may also comprise an anchor 72 and an anchor cable 82. The anchor cable 82 may be attached to the anchor 72, wherein the anchor cable 82 may be used for deploying the anchor 72 within the LAA wall 66. The anchor cable 82 may be a hollow coaxial cable standardly used in the industry. The anchor cable 82 and anchor 72 may encompass the delivery wire 60 and/or buddy wire 62, wherein the delivery wire 60 and/or buddy wire 62 may traverse through an inner lumen of the anchor 72 and an inner lumen of the anchor cable 82. The delivery wire 60 may be used to navigate the anchoring system 50 through the LAA 64. The buddy wire 62 may remain inside the pericardial space 68 and is a safety feature in case of emergencies. The buddy wire 62 allows an interventional cardiologist to advance another catheter through the LAA wall 66 and place a plug within the small hole 70 if a malfunction is observed with the anchor 72 or the occluder device 80. Alternatively, the delivery wire 70 and buddy wire 72 may be retrieved and the anchor 72 and anchor cable 82 advanced through the delivery catheter 58 into the pericardial space 68 without using the delivery wire 60. As shown in FIG. 3B, the anchor 72 may be integral with the occluder device 80. In this aspect, the anchor cable 82 may be used for deploying the anchor 72 within the LAA wall 66 and for deploying and retrieving the occluder device 80 within the LAA 64, wherein the occluder cable 84 is not utilized.

Figure 4A:
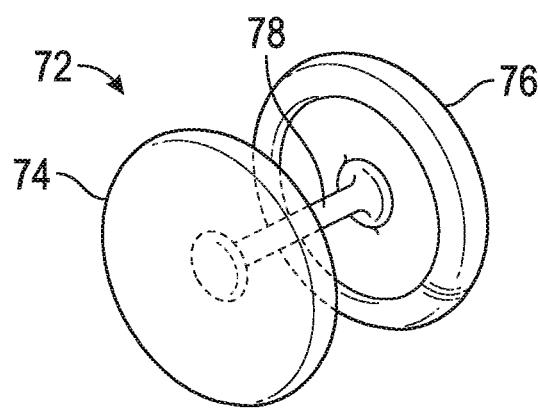
FIG. 4A is a frontal-side view of the anchor of the anchoring system and method of FIG. 2, wherein the anchor is in a deployed second position comprising a sheave shape with a first half, a second half, and a shaft connecting the two halves.
Figure 4B:
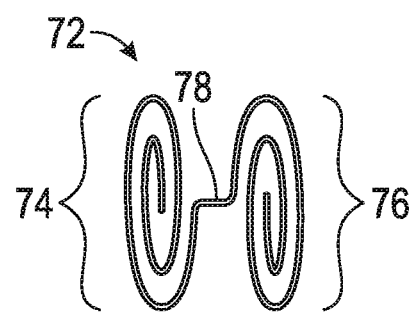
FIG. 4B is a frontal side-view of the anchor of the anchoring system and method of FIG. 2, wherein the anchor is in a deployed second position comprising a double-coiled shape with a first half, a second half, and a shaft connecting the two halves.

Illustrated in FIGS. 4A and 4B, the anchor 72 may comprise a first half 74, a second half 76, and a shaft 78 connecting the first half 74 to the second half 76. In particular, the anchor 72 may be shaped like a sheave (FIG. 4A) or a double-coil (FIG. 4B), although it is contemplated that other anchor shapes may also be utilized in the present invention. The particular coils of the double-coil anchor 72 may both unwind in opposite directions as depicted in FIG. 4B. When unwinding in opposite directions (e.g., clockwise and counter-clockwise) there will be counter-forces acting on the coils to prevent the anchor 72 from unraveling while deployed within the LAA wall 66. Alternatively, the particular coils of the double-coil anchor 72 may both unwind in the same direction (not shown). The anchor 72 may be comprised of wire and/or wire mesh having a square, rectangle, flat, sphere, circle, oval, pentagon, octagon, or any other shape, and may be comprised of single or multiple wires. The anchor 72 may be circular in diameter, however, it is contemplated that other cross-sectional shapes may also be utilized, including but not limited to, square, rectangular, triangular, pentagonal, and octagonal depending on the manufacturing technique. The anchor 72 may be comprised of stainless steel, platinum, Nitinol, Elgiloy or other materials standardly used in the industry. The anchor 72 may also comprise antibiotics, drugs that prevent the LAA pericardium wall from bleeding, ePTFE, any variety of materials which facilitate cellular in-growth, hydrogel, anticoagulants, fibrin hairs and/or other pharmaceuticals. The anchor 72 may have a lumen wherein the delivery wire 60 traverses therein, alternatively, the anchor 72 may not have a lumen. The anchor 72 may further include barbs, points, bristles, spurs, screws, hooks, pins, sutures, adhesives, pledgets, or other means of attachment.

Figure 4C:
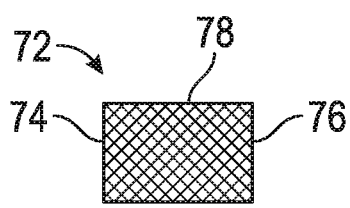
FIG. 4C is a side-view of the anchor of FIGS. 4A and 4B, wherein the anchor is in a contracted first position.

Illustrated in FIGS. 4A, 4B and 4C, the anchor 72 may have a contracted first position (FIG. 4C) and a deployed second position (FIGS. 4A, 4B). In the contracted first position (FIG. 4C), the first half 74, second half 76, and shaft 78 of the anchor 72 have a diameter of approximately 0.5-5 mm and a length of approximately 2-55 mm. In the deployed second position (FIG. 4A, 4B), the first half 74 and second half 76 of the anchor 72 may expand outwards a distance of approximately 5-25 mm in diameter, wherein the shaft 78 remains approximately 0.5-5 mm in diameter. The anchor 72 may self-expand from the contracted first position (FIG. 4C) to the deployed second position (FIG. 4A, 4B).

Figure 4D:
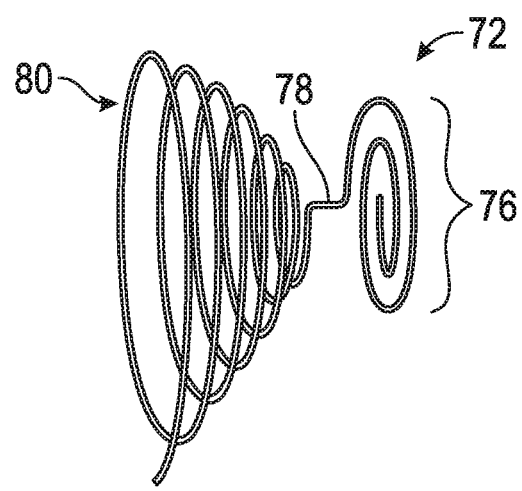
FIG. 4D is a frontal side-view of the anchor of the anchoring system and method of FIG. 2, wherein the occluder device and the anchor are integral.
Figure 5A:
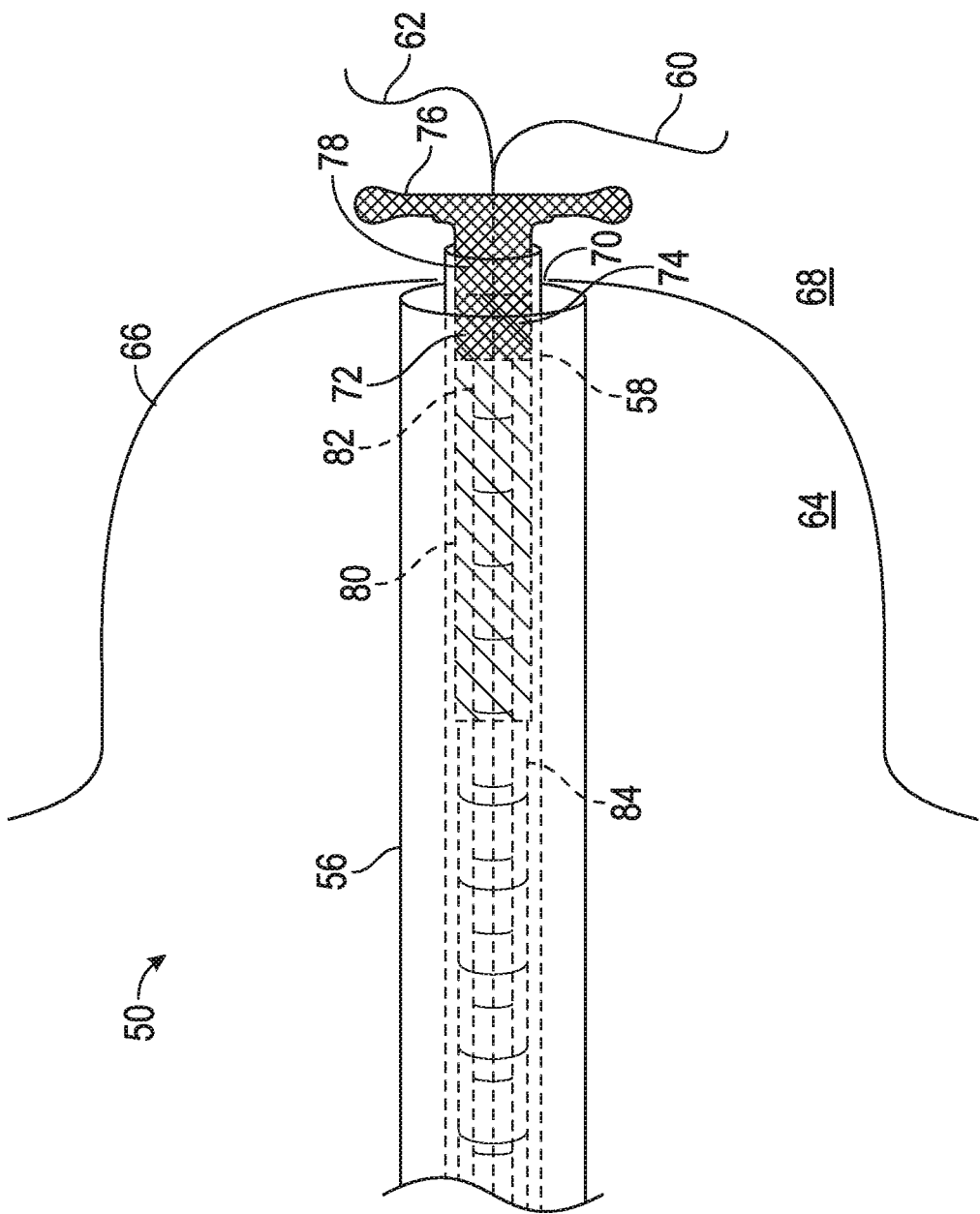
FIG. 5A is a view of the anchoring system and method of FIG. 2, wherein the second half of the anchor is deployed in the pericardial space.
Figure 5B:
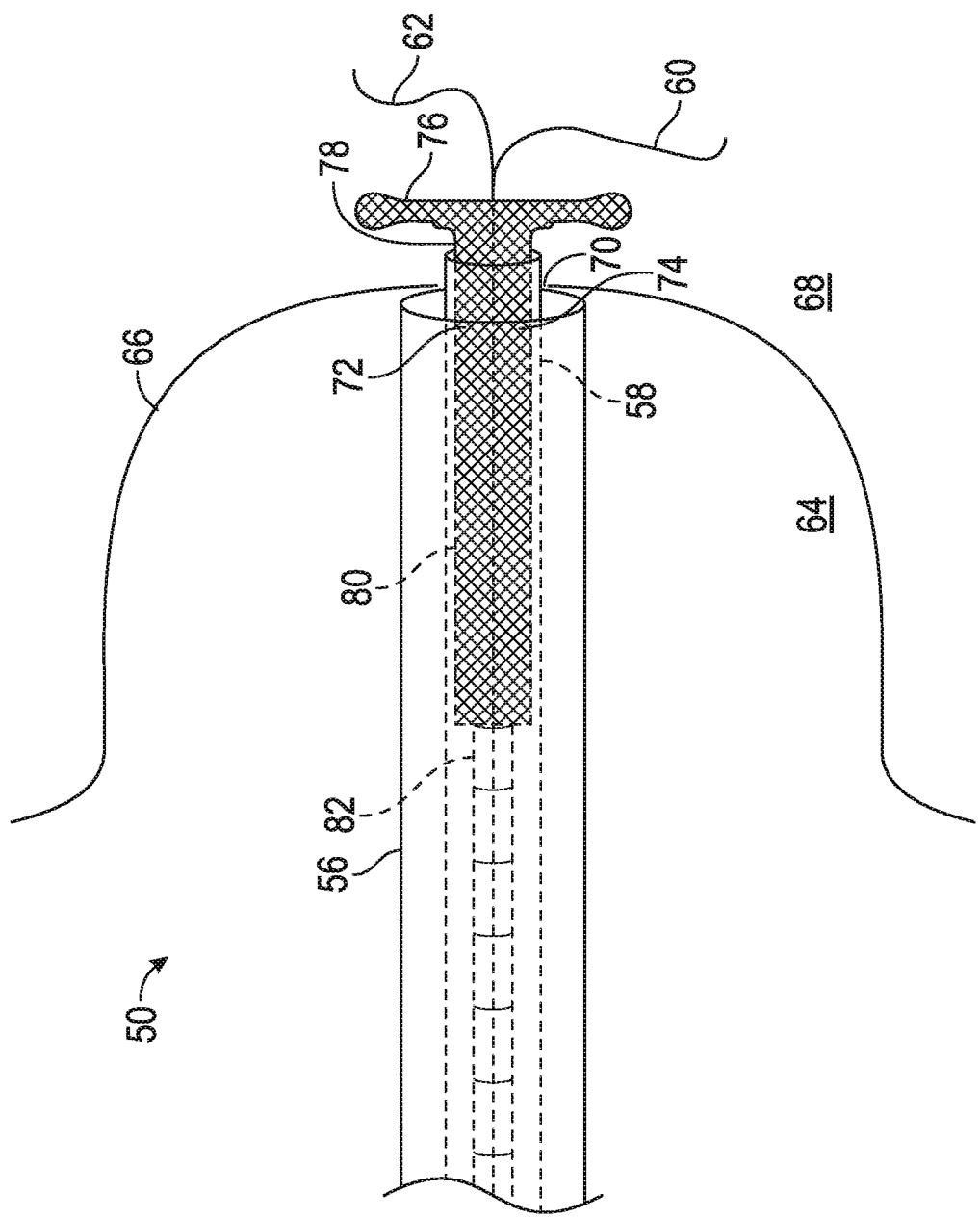
FIG. 5B is a view the anchoring system and method of FIG. 5A, wherein the occluder device and anchor are integral.

Alternatively as illustrated in FIG. 4D, the anchor 72 may be integral with the occluder device 80. As shown in FIG. 4D, the first half 74 of the anchor is connected to and formed integrally with the occluder device 80. However, it is contemplated by the present invention that either half 74, 76 of the anchor may be formed integrally with the occluder device 80 as needed.

illustrated in FIG. 5A, the anchor 72 in the contracted first position (FIG. 4C) may be advanced through the delivery catheter 58 using the anchor cable 82 and the delivery wire 60, wherein the anchor 72 extends into the pericardial space 68. The delivery catheter 58 may then be retracted, allowing the second half 76 of the anchor 72 to self-expand from the contracted first position to the deployed second position within the pericardial space 68. While the second half 76 of the anchor 72 is in the deployed second position, the occluder device 80 including the shaft 78 and the first half 74 of the anchor 72 remain temporarily inside the delivery catheter 58. Alternatively as shown in FIG. 5B, the anchor 72 and occluder device 80 may be integral, wherein the integral anchor 72 in the contracted first position (FIG. 4C) may be advanced through the delivery catheter 58 using the anchor cable 82 and the delivery wire 60, wherein the anchor 72 extends into the pericardial space 68 using the system 50 of the present invention described above.

Figure 6A:
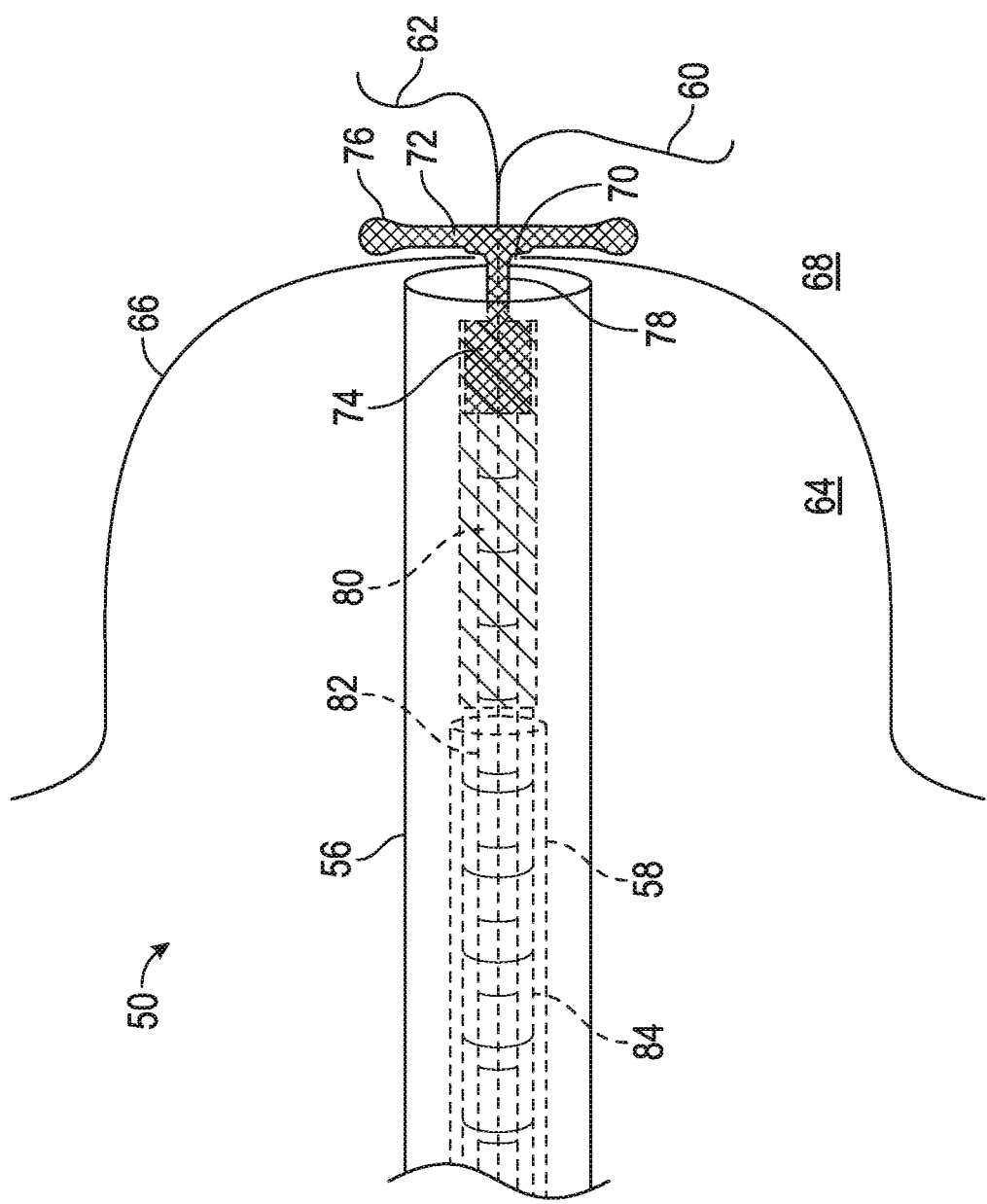
FIG. 6A is a view of the anchoring system and method of FIG. 2, wherein the first half of the anchor is partially deployed in the occluder device.
Figure 6B:
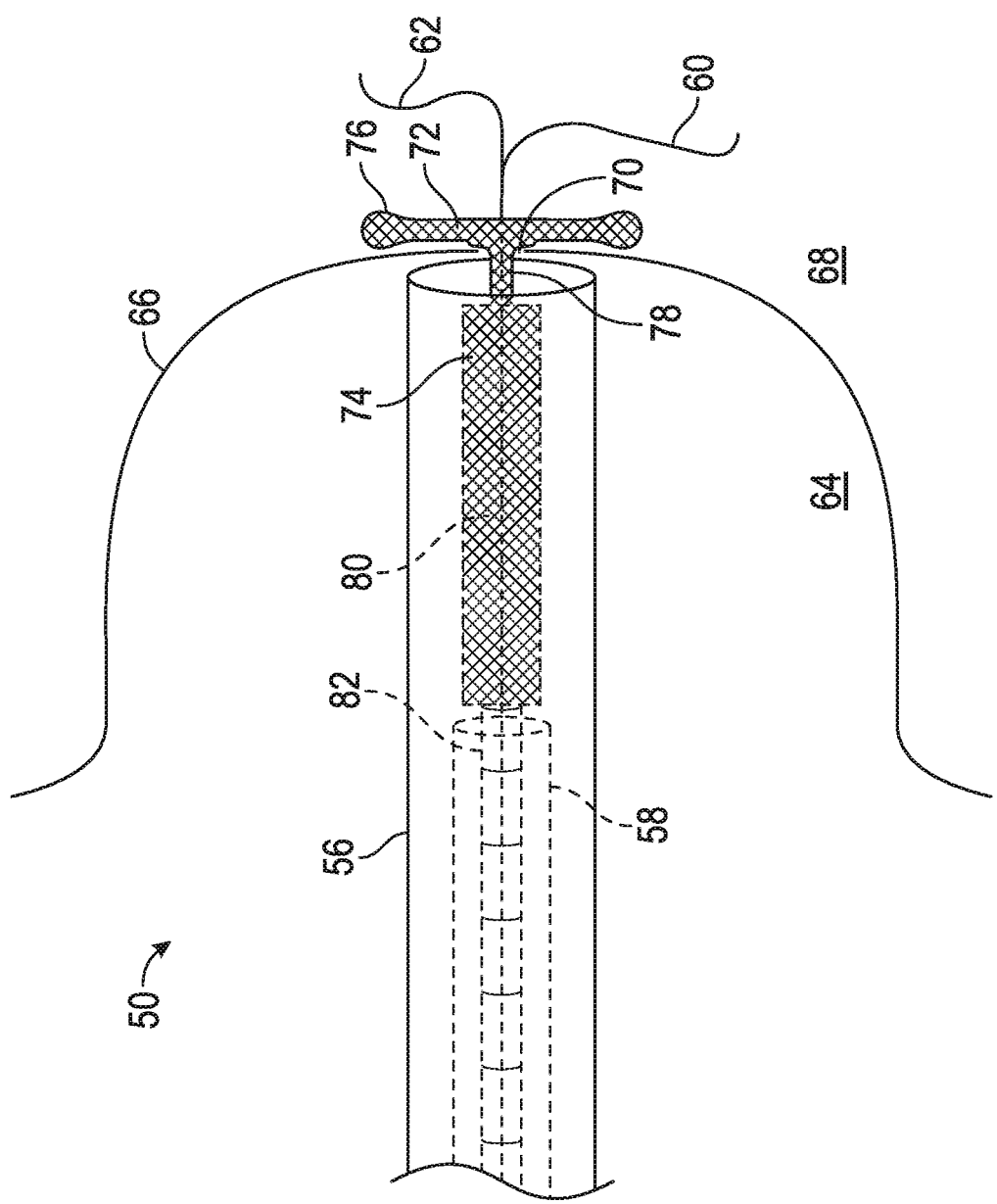
FIG. 6B is a view the anchoring system and method of FIG. 6A, wherein the occluder device and anchor are integral.

Illustrated in FIG. 6A, the delivery catheter 58 may be further retracted, allowing the first half 74 of the anchor 72 to self-expand from the contracted first position to a partially deployed second position within the occluder device 80, wherein the occluder device 80 remains inside the outer sheath 56. The shaft 78 resides inside the inner endocardium layer, middle myocardium layer, and outer epicardium layer of the LAA wall 66. The second half 76 of the anchor 72 remains in the deployed second position within the pericardial space 68, wherein the first half 74 of the anchor 72 is in the partially deployed second position within the occluder device 80. Alternatively as shown in FIG. 6B, the anchor 72 and occluder device 80 may be integral, wherein the integral anchor 72 and occluder device 80 may be advanced together through the delivery catheter 58, wherein the anchor 72 is implanted in the LAA wall 66 using the system 50 of the present invention described above.

Figure 7A:
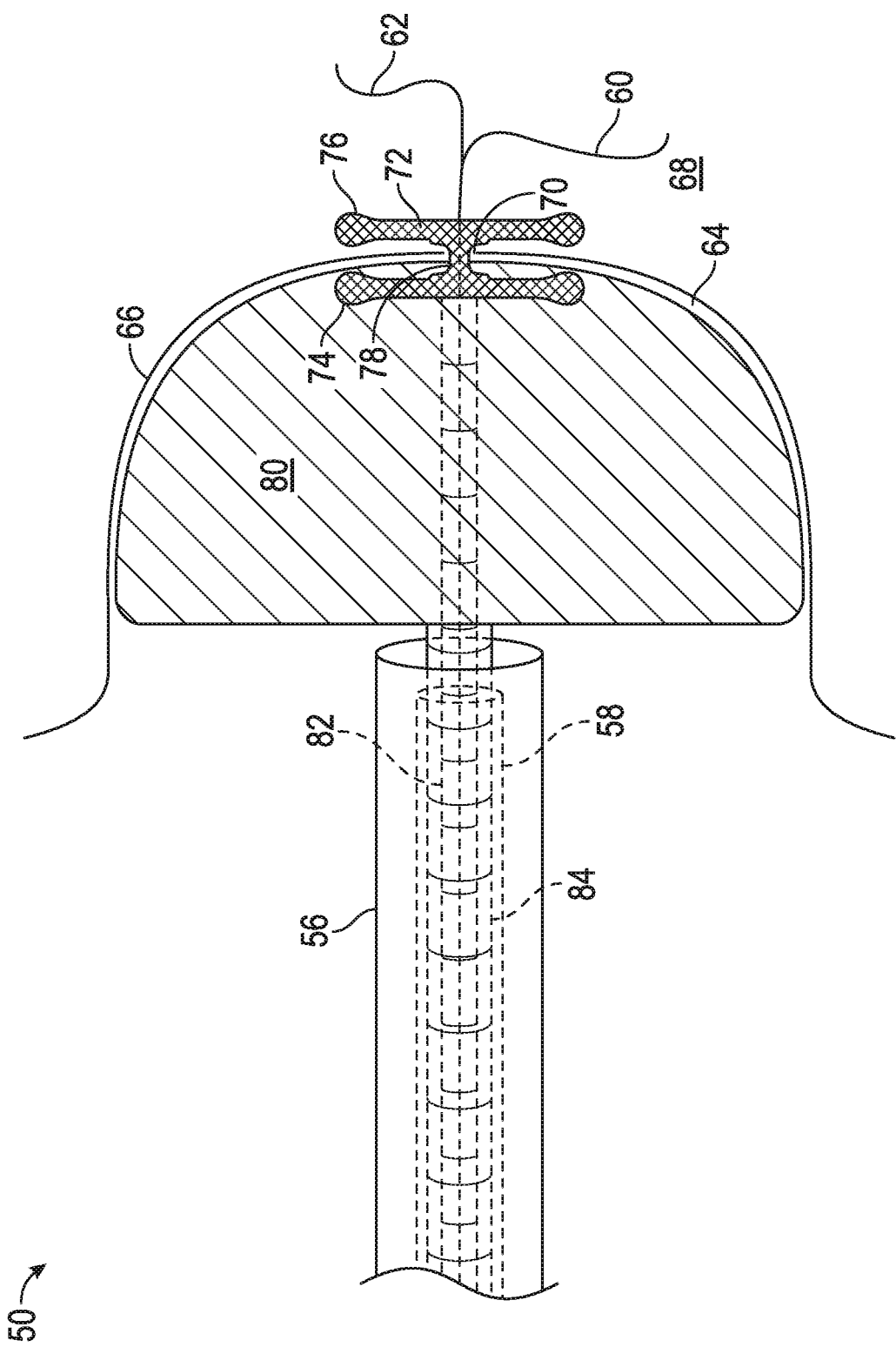
FIG. 7A is a view of the anchoring system and method of FIG. 2, wherein the occluder device is released from the outer sheath and the second half of the anchor fully deployed to pin the occluder device against the LAA wall.
Figure 7B:
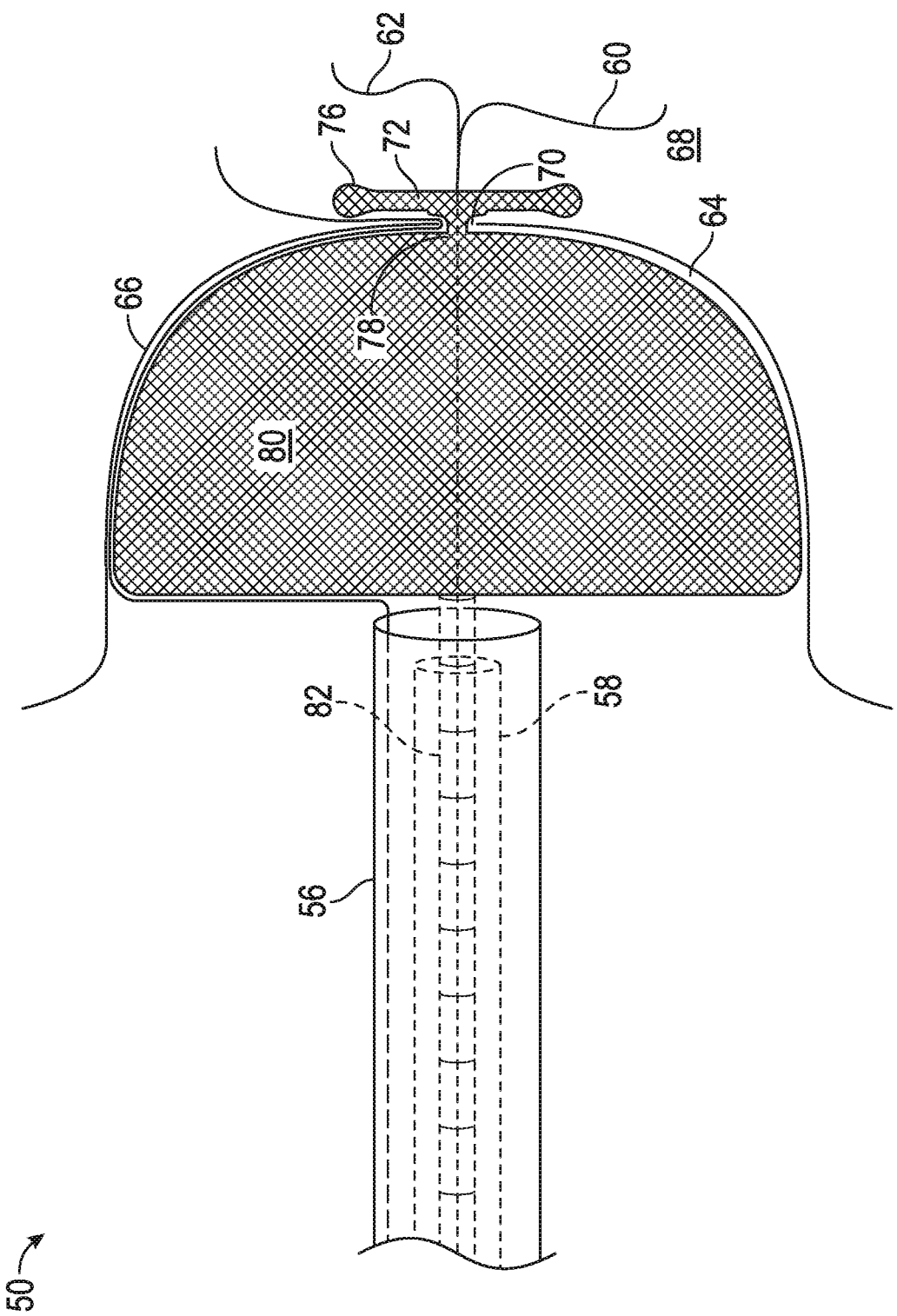
FIG. 7B is a view the anchoring system and method of FIG. 7A, wherein the occluder device and anchor are integral.

Illustrated in FIG. 7A, the outer sheath 56 may be retracted to allow the occluder device 80 to expand inside the LAA 64. Moreover, retracting the outer sheath 56 allows the first half 74 of the anchor 72 to fully expand into the deployed second position within the occluder device 80. Thus, the shaft 78 of the anchor 72 may extend through the hole in the distal end of the occluder device 80, wherein the distal end of the occluder device 80 pinches down on the shaft 78. Furthermore, the first half of the anchor 74 in the deployed second position may pin the occluder device 80 against the LAA wall 66, wherein the anchor 72 effectively moors the occluder device 80 inside the LAA 64. At this time the expanded anchor 72 in the deployed second position covers a large surface area and therefore retains the occluder device 80 in an implanted position within the LAA 64. Alternatively as shown in FIG. 7B, the anchor 72 and occluder device 80 may be integral. By anchoring the occluder device 80 via the anchor 72 through all three layers of the LAA wall 66 instead of merely latching onto the thin endocardium layer the anchoring system 50 of the present invention lowers the risk of embolization. Here, the anchor cable 82 remains attached to the anchor 72 and the occluder device 80 in case problems arise after deployment of the occluder device 80. If no problems arise and it is determined that the occluder device 80 is in an optimal location of the LAA 64, the anchor cable 82 may be detached from the occluder device 80 and the anchor 72 and removed from the LAA 64.

The buddy wire 62 and delivery wire 60 may also be withdrawn from the LAA 64, leaving the occluder device 80 anchored securely in the LAA 64 by the anchoring system 50 of the present invention.

Figure 8:
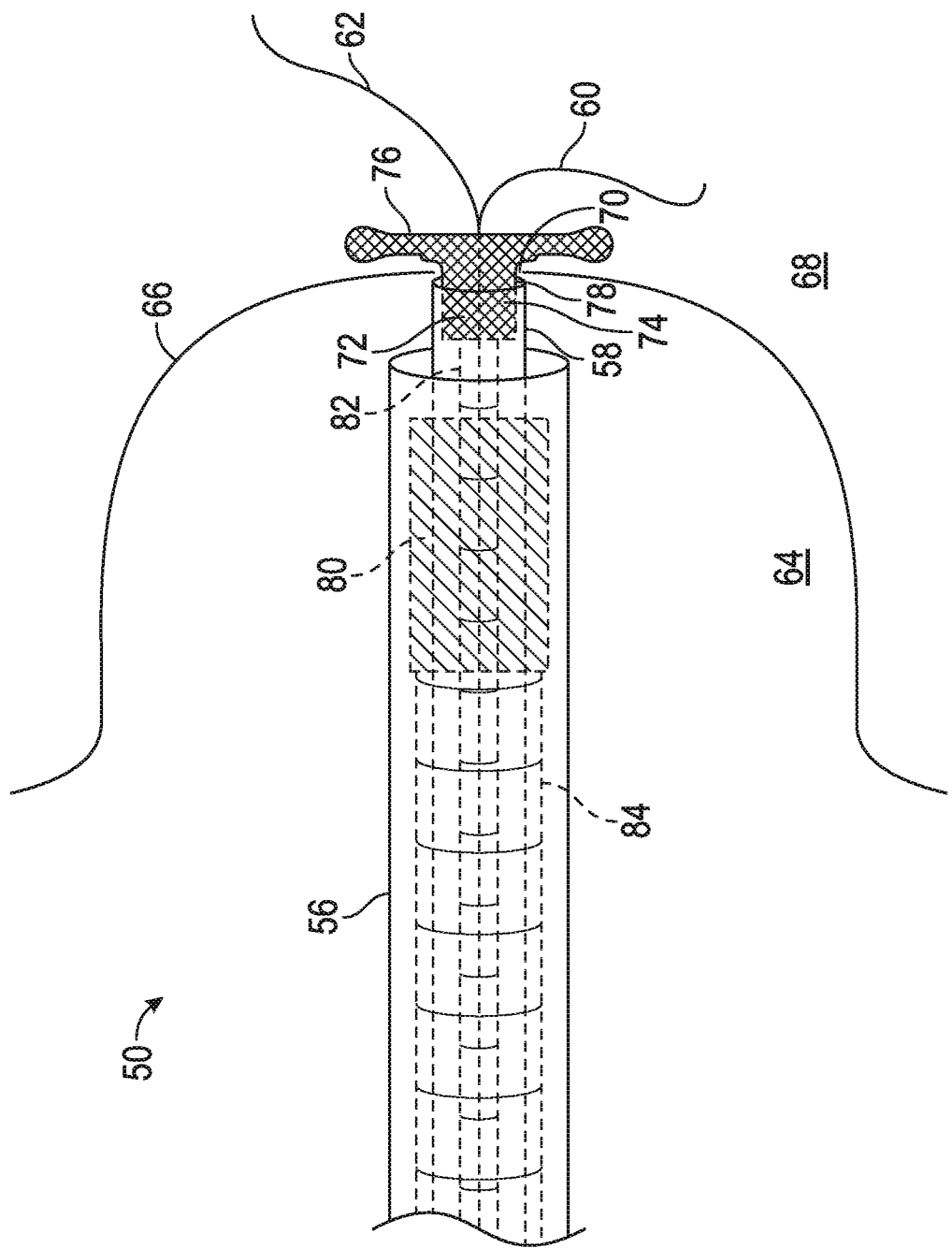

FIG. 8 illustrates the anchoring system 50 of the present invention if problems arise after deployment of the occluder device 80. For instance, it may be determined that the occluder device 80 is not placed in an optimal location of the LAA 64 after deployment to achieve maximum occlusion. In this situation prior to release of the occluder cable 84 from the occluder device 80 and the anchor cable 82 from the anchor 72 the outer sheath 56 may be advanced over the occluder device 80 to the LAA wall 66, wherein the occluder device 80 is retracted inside the outer sheath 56 using the occluder cable 82. The delivery catheter 58 may then be advanced to the LAA wall 66, wherein the occluder device 80 and the first half 74 of the anchor 72 is retracted inside the delivery catheter 58 using the anchor cable 82. Thus, using the anchor cable 82, the first half 74 of the anchor 72 retracts from the deployed second position to the contracted first position to fit inside the delivery catheter 58 along with the occluder device 80. The occluder device 80 may then be removed from the LAA 64, or the occluder device 80 may be re-deployed in a more optimal location of the LAA 64. If the occluder device 80 is removed from the LAA 64, the first half 74 of the anchor 72 may be allowed to expand from the contracted first position to the deployed second position within the LAA 64. Thus, the deployed anchor 72 remains inside the LAA 64 and allows for occlusion of the small hole 70 that was created by the delivery catheter 58 through the inner endocardium layer, middle myocardium layer, and outer epicardium layer of the LAA wall 66. Alternatively, if the anchor 72 and the occluder device 80 are integral both may be removed simultaneously from the LAA 64 using the anchor cable 82 via the delivery catheter 58.

Figure 9:
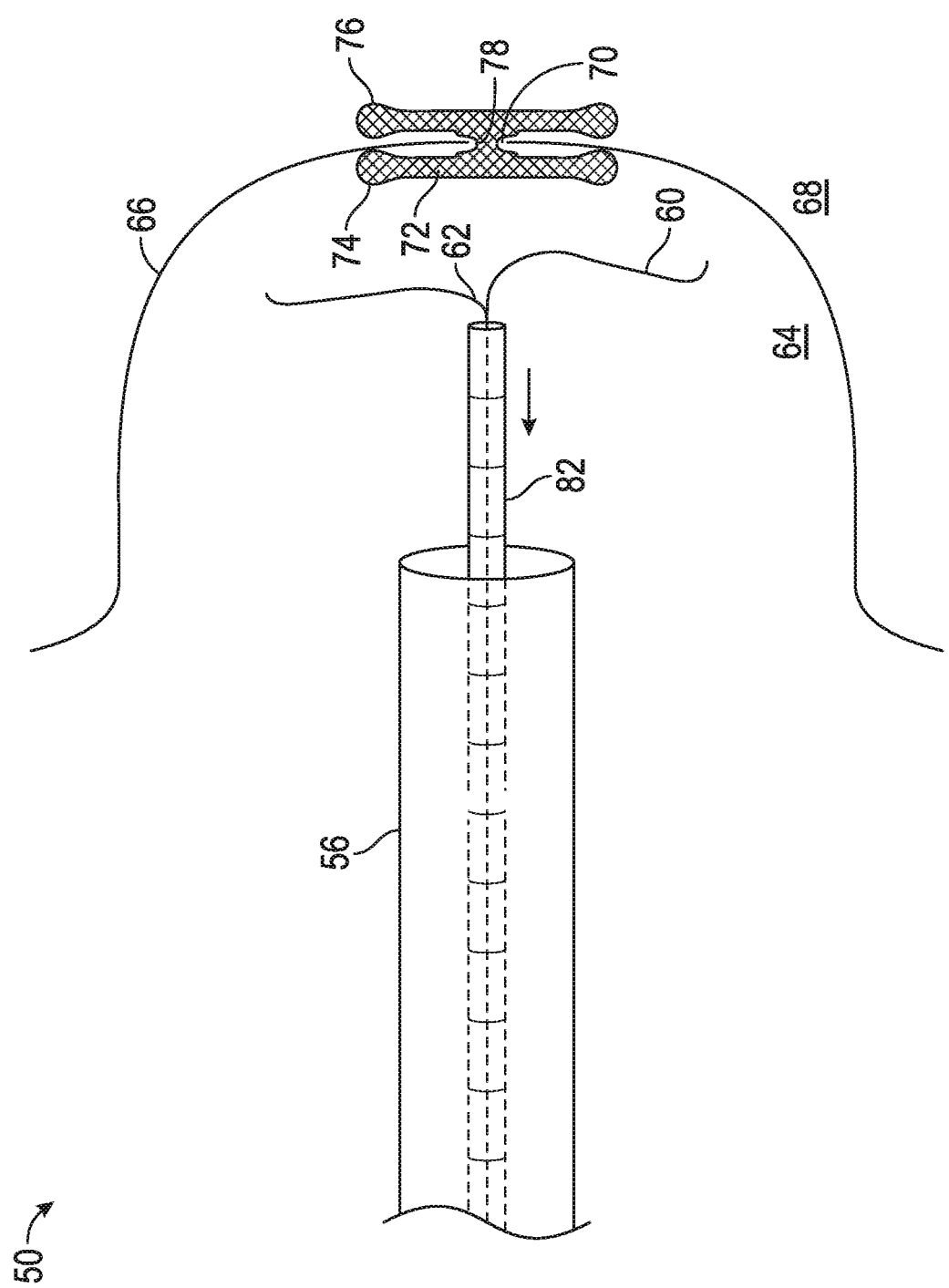

Illustrated in FIG. 9, if optimal placement of the occluder device 80 was not achieved the anchor 72 may be released from the anchor cable 82 and deployed alone within the LAA wall 66 to plug the small hole 70 and prevent fluids from entering the pericardial space 68. The delivery wire 60 and buddy wire 62 may be subsequently removed from the LAA 64. This allows for a new anchor 72 to be placed within the LAA wall 66 using the anchoring system 50 cited above for achieving optimal placement of the occluder device 80 within the LAA 64. On the other hand, if the anchor 72 is initially placed in an optimal location within the wall 66 but there are problems with the occluder device 80, a second occluder device may be advanced with the delivery catheter 58 and deployed within the LAA 64 using the anchoring system 50 cited above. Thus, the anchoring system 50 of the present invention allows an interventional cardiologist to quickly and cost-effectively implant the occluder device 80 into the LAA 64 using anchor 72, safely retrieve or re-deploy the occluder device 80 if initial placement was improper or if complications arise, with an option to re-implant a new occluder device and new anchor in an optimal location of the LAA 24, After optimal placement of the occluder device 80 within the LAA 64 is achieved, the delivery wire 60 and buddy wire 62 may be removed from the LAA 64.

In another aspect of the present invention, an anchor 72 is provided depicted in FIGS. 4A. 4B, 4C and 4D for anchoring an occluder device 80 within a LAA 64 using the anchoring system 50 as explained above.

In yet another aspect of the present invention, a method of implanting and retrieving an occluder device within a LAA is illustrated in FIGS. 1-9. The method of the present invention comprises providing anchoring system 50 as explained above. The method of the present invention further comprises inserting the outer sheath 56 into the LAA 64 via the left atrium proper of the heart by crossing the atrial septum using a transeptal procedure as depicted in FIG. 1. If a balloon-occlusion catheter has been utilized, the balloon occlusion may be expanded to occlude the LAA 64 from the left atrium proper. Expanding the balloon occlusion may improve stabilization of the outer sheath 56 within the LAA 64 and allow for better imaging of the LAA 64 by an interventional cardiologist.

illustrated in FIG. 2, the method of the present invention further comprises providing a delivery catheter 58 and an optional inner dilator 86, wherein the inner dilator 86 includes a pointed distal end 88. The delivery catheter 58 and inner dilator 86 may be configured to encompass a delivery wire 60 and/or a buddy wire 62, wherein the delivery wire 60 and buddy wire 62 may traverse through an inner lumen of the delivery catheter 58 and inner dilator 86. The delivery wire 60 and/or buddy wire 62 may be of types standardly used in the industry, wherein a diameter of the delivery wire 60 may range between approximately 0.025-0.052 inches and a diameter of the buddy wire 62 may range between approximately 0.008-0.025 inches. The delivery catheter 58 and the inner dilator 86 may be advanced through the outer sheath 56 to the LAA wall 66. Using the pointed distal end 88 of the inner dilator 86, the inner dilator 86 and the delivery catheter 58 may be further advanced through the inner endocardium layer, middle myocardium layer, and outer epicardium layer to penetrate the LAA wall 66 and create a small hole 70. Thus, the pointed distal end 88 of the inner dilator 86, along with a distal end of the delivery catheter 58, extends into the pericardial space 68. When utilized, the inner dilator 86 may be subsequently removed from the delivery catheter 58, wherein the distal end of the delivery catheter 58 remains extending into the pericardial space 68. Alternatively, when the inner dilator 86 is not being utilized the delivery catheter 58 may be advanced through the inner endocardium layer, middle myocardium layer, and outer epicardium layer to penetrate the of the LAA wall 66 and create small hole 70.

Illustrated in FIG. 3A, the method of the present invention further comprises providing an occluder device 80 and an occluder cable 84. It is contemplated that the method of the present invention may be used with a diverse range of LAA occluder devices 80 such as coil implants, foam plugs, expandable frames, combinations thereof, and other occluder devices currently used in the industry and/or to be developed in the future. Specific examples of occluder devices 80 that may be used by the present invention include, but are not limited to, WATCHMAN®, ATRIUM®, PLAATO LAA Occlusion System®, AMPLATZER™, and AMULET™. In the present invention, the occluder device 80 may have a distal end with a hole approximately 1-5 mm in diameter.

As shown in FIG. 3A, the occluder cable 84 may be a hollow coaxial cable standardly used in the industry. The occluder cable 84 may be attached to the occluder device 80, wherein the occluder cable 84 may be used for deploying and retrieving the occluder device 80 within the LAA 64. The occluder device 80 and the occluder cable 84 may reside inside the delivery catheter 58. As further shown in FIGS. 3 and 3A, the method of the present invention further comprises providing an anchor 72 and an anchor cable 82, wherein the anchor 72 and anchor cable 82 are inserted in the delivery catheter 58. The anchor cable 82 may be attached to the anchor 72, wherein the anchor cable 82 may be used for deploying the anchor 72 within the LAA wall 66. The anchor cable 82 may be a hollow coaxial cable standardly used in the industry. The anchor cable 82 and anchor 72 may encompass the delivery wire 60 and/or buddy wire 62, wherein the delivery wire 60 and/or buddy wire 62 may traverse through an inner lumen of the anchor 72 and an inner lumen of the anchor cable 82. The delivery wire 60 may be used to navigate the anchoring system 50 through the LAA 64. Alternatively, the anchor 72 and anchor cable 82 may be advanced through the delivery catheter 58 into the pericardial space 68 without using the delivery wire 60. The buddy wire 62 may remain inside the pericardial space 68 and is a safety feature in case of emergencies. The buddy wire 62 allows an interventional cardiologist to advance another catheter through the LAA wall 66 and place a plug within the small hole 70 if a malfunction is observed with the anchor 72 or the occluder device 80. Alternatively as shown in FIG. 313, the anchor 72 may be integral with the occluder device 80. In this aspect, the anchor cable 82 may be used for deploying the anchor 72 within the LAA wall 66 and for deploying and retrieving the occluder device 80 within the LAA 64, wherein the occluder cable 84 is not utilized.

Illustrated in FIGS. 4A and 4B, the anchor 72 may comprise a first half 74, a second half 76, and a shaft 78 connecting the first half 74 to the second half 76. In particular, the anchor 72 may be shaped like a sheave (FIG. 4A) or a double-coil (FIG. 4B), although it is contemplated that other anchor shapes may also be utilized in the present invention. The particular coils of the double-coil anchor 72 may both unwind in opposite directions as depicted in FIG. 4B. When unwinding in opposite directions (e.g., clockwise and counter-clockwise) there will be counter-forces acting on the coils to prevent the anchor 72 from unraveling while deployed within the LAA wall 66. Alternatively, the particular coils of the double-coil anchor 72 may both unwind in the same direction (not shown). The anchor 72 may be comprised of wire and/or wire mesh having a square, rectangle, flat, sphere, circle, oval, pentagon, octagon, or any other shape, and may be comprised of single or multiple wires. The anchor 72 may be circular in diameter, however, it is contemplated that other cross-sectional shapes may also be utilized, including but not limited to, square, rectangular, triangular, pentagonal, and octagonal depending on the manufacturing technique. The anchor 72 may be comprised of stainless steel, platinum, Nitinol, Elgiloy or other materials standardly used in the industry. The anchor 72 may also comprise antibiotics, drugs that prevent the LAA pericardium wall from bleeding, ePTFE, any variety of materials which facilitate cellular in-growth, hydrogel, anticoagulants, fibrin hairs and/or other pharmaceuticals. The anchor 72 may have a lumen wherein the delivery wire 60 traverses therein, alternatively, the anchor 72 may not have a lumen. The anchor 72 may further include barbs, points, bristles, spurs, screws, hooks, pins, sutures, adhesives, pledgets, or other means of attachment.

Illustrated in FIGS. 4A, 4B and 4C, the anchor 72 may have a contracted first position (FIG. 4C) and a deployed second position (FIG. 4A, 4B). In the contracted first position (FIG. 4C), the first half 74, second half 76, and shaft 78 of the anchor 72 have a diameter of approximately 0.5-5 mm and a length of approximately 2-55 mm. In the deployed second position (FIG. 4A, 4B), the first half 74 and second half 76 of the anchor 72 may expand outwards a distance of approximately 5-25 mm in diameter, wherein the shaft 78 remains approximately 0.5-5 mm in diameter. The anchor 72 may self-expand from the contracted first position (FIG. 4C) to the deployed second position (FIG. 4A, 4B). Alternatively as illustrated in FIG. 4D, the anchor 72 may be integral with the occluder device 80. As shown in FIG. 4D, the first half 74 of the anchor is connected to and formed integrally with the occluder device 80. However, it is contemplated by the present invention that either half 74, 76 of the anchor may be formed integrally with the occluder device 80 as needed.

illustrated in FIG. 5A, the method of the present invention comprises advancing the anchor 72 in the contracted first position (FIG. 4A) through the delivery catheter 58 using the anchor cable 82 and the delivery wire 60, wherein the anchor 72 extends into the pericardial space 68. The delivery catheter 58 may then be retracted, allowing the second half 76 of the anchor 72 to self-expand from the contracted first position to the deployed second position within the pericardial space 68. While the second half 76 of the anchor 72 is in the deployed second position, the occluder device 80 including the shaft 78 and the first half 74 of the anchor 72 remain temporarily inside the delivery catheter 58. Alternatively as shown in FIG. 5B, the anchor 72 and occluder device 80 may be integral, wherein the integral anchor 72 in the contracted first position (FIG. 4C) may be advanced through the delivery catheter 58 using the anchor cable 82 and the delivery wire 60, wherein the anchor 72 extends into the pericardial space 68 using the system 50 of the present invention described above.

Illustrated in FIG. 6A, the method of the present invention further comprises retracting the delivery catheter 58, allowing the first half 74 of the anchor 72 to self-expand from the contracted first position to a partially deployed second position within the occluder device 80, wherein the occluder device 80 remains inside the outer sheath 56. The shaft 78 resides inside the inner endocardium layer, middle myocardium layer, and outer epicardium layer of the LAA wall 66. The second half 76 of the anchor 72 remains in the deployed second position within the pericardial space 68, wherein the first half 74 of the anchor 72 is in the partially deployed second position within the occluder device 80. Alternatively as shown in FIG. 6B, the anchor 72 and occluder device 80 may be integral, wherein the integral anchor 72 and occluder device 80 may be advanced together through the delivery catheter 58, wherein the anchor 72 is implanted in the LAA wall 66 using the system 50 of the present invention described above.

Illustrated in FIG. 7A, the method of the present invention comprises retracting the outer sheath 56 to allow the occluder device 80 to expand inside the LAA 64. Moreover, retracting the outer sheath 56 allows the first half 74 of the anchor 72 to fully expand into the deployed second position within the occluder device 80. Thus, the shaft 78 of the anchor 72 may extend through the hole in the distal end of the occluder device 80, wherein the distal end of the occluder device 80 pinches down on the shaft 78. Furthermore, the first half of the anchor 74 in the deployed second position may pin the occluder device 80 against the LAA wall 66, wherein the anchor 72 effectively moors the occluder device 80 inside the LAA 64. At this time the expanded anchor 72 in the deployed second position covers a large surface area and therefore retains the occluder device 80 in an implanted position within the LAA 64. Alternatively as shown in FIG. 7B, the anchor 72 and occluder device 80 may be integral. By anchoring the occluder device 80 via the anchor 72 through all three layers of the LAA wall 66—instead of merely latching onto the thin endocardium layer—the method of the present invention lowers the risk of embolization. Here, the anchor cable 82 remains attached to the anchor 72 and the occluder device 80 in case problems arise after deployment of the occluder device 80. If no problems arise and it is determined that the occluder device 80 is in an optimal location of the LAA 64, the anchor cable 82 may be detached from the occluder device 80 and the anchor 72 and removed from the LAA 64. The buddy wire 62 and delivery wire 60 may also be withdrawn from the LAA 64, leaving the occluder device 80 anchored securely in the LAA 64 by the method of the present invention.

FIG. 8 illustrates the method of the present invention if problems arise after deployment of the occluder device 80. For instance, the method comprises making a determination that the occluder device 80 is not placed in an optimal location of the LAA 64 after deployment to achieve maximum occlusion. In this situation—prior to release of the occluder cable 84 from the occluder device 80 and the anchor cable 82 from the anchor 72—the outer sheath 56 may be advanced over the occluder device 80 to the LAA wall 66, wherein the occluder device 80 is retracted inside the outer sheath 56 using the occluder cable 82. The delivery catheter 58 may then be advanced to the LAA wall 66, wherein the occluder device 80 and the first half 74 of the anchor 72 is retracted inside the delivery catheter 58 using the anchor cable 82. Thus, using the anchor cable 82, the first half 74 of the anchor 72 retracts from the deployed second position to the contracted first position to fit inside the delivery catheter 58 along with the occluder device 80. The occluder device 80 may then be removed from the LAA 64, or the occluder device 80 may be re-deployed in a more optimal location of the LAA 64. If the occluder device 80 is removed from the LAA 64, the first half 74 of the anchor 72 may be allowed to expand from the contracted first position to the deployed second position within the LAA 64. Thus, the deployed anchor 72 remains inside the LAA 64 and allows for occlusion of the small hole 70 that was created by the delivery catheter 58 through the inner endocardium layer, middle myocardium layer, and outer epicardium layer of the LAA wall 66. Alternatively, if the anchor 72 and the occluder device 80 are integral both may be removed simultaneously from the LAA 64 using the anchor cable 82 via the delivery catheter 58.

Illustrated in FIG. 9, if a determination is made that optimal placement of the anchor 72 was not achieved, the anchor 72 may be released from the anchor cable 82 and deployed alone within the LAA wall 66 to plug the small hole 70 and prevent fluids from entering the pericardial space 68. The delivery wire 60 and buddy wire 62 may be subsequently removed from the LAA 64. This allows for a new anchor 72 to be placed within the LAA wall 66 using the method cited above for achieving optimal placement of the occluder device 80 within the LAA 64. On the other hand, if a determination is made that the anchor 72 is initially placed in an optimal location within the LAA wall 66 but there are problems with the occluder device 80, a second occluder device may be advanced with the delivery catheter 58 and deployed within the LAA 64 using the method cited above. Thus, the method of the present invention allows an interventional cardiologist to quickly and cost-effectively implant the occluder device 80 into the LAA 64 using anchor 72, safely retrieve or re-deploy the occluder device 80 if initial placement was improper or if complications arise, with an option to re-implant a new occluder device and new anchor in an optimal location of the LAA 24. After optimal placement of the occluder device 80 within the LAA 64 is achieved, the delivery wire 60 and buddy wire 62 may be removed from the LAA 64.

The anchoring system and method of the present invention are universally applicable to occluder devices of all shapes and sizes, makes, models, and manufacturers. It is also intended that the anchoring system and method of the present invention may be used for other medical devices to be implanted in the cardiac or vascular system. For example, the anchoring system and method of the present invention may be used to implant medical devices that collect physiologic parameters inside the main or branch pulmonary arteries, the right or left ventricle or other intracardiac structures (e.g., atrial septum, aorta, etc.). Thus, using techniques described above various medical devices may be anchored in a free wall of an arterial, atrial or ventricular wall. While intended for humans, the anchoring system and method of the present invention may also be used for all manner of animals. Although the invention has been described and illustrated with respect to preferred aspects thereof, it is not to be so limited since changes and modifications may be made therein which are within the full intended scope of the invention.

What is claimed is:

1. An anchoring system for implanting a left atrial appendage (LAA) occluder device within the LAA of a heart, comprising:
   the LAA occluder device;
   an anchor comprising a first half, an opposite second half and a shaft connecting the first half to the second half;
   a contracted first position of the anchor;
   a deployed second position of the anchor;
   the LAA occluder device in a retracted condition and the anchor in the contracted first position configured to be advanced into the LAA;
   the second half and the shaft of the anchor in the contracted first position configured to be advanced through a hole through an inner endocardium layer, a middle myocardium layer, and an outer epicardium layer of a LAA wall;
   the second half of the anchor in the contracted first position configured to be advanced into a pericardial space;
   the second half of the anchor configured to expand from the contracted first position to the deployed second position in the pericardial space;
   the shaft of the anchor configured to reside inside the hole through the inner endocardium layer, the middle myocardium layer, and the outer epicardium layer of the LAA wall;
   the first half of the anchor configured to expand from the contracted first position to a partially deployed second position within the LAA occluder device;
   the LAA occluder device configured to expand and occlude the LAA;
   the first half of the anchor configured to expand from the partially deployed second position to the deployed second position within the LAA occluder device; and
   the anchor configured to pin the LAA occluder device between the first half of the anchor in the deployed second position and against the LAA wall inside the LAA;
   wherein the LAA occluder device is configured to be moored to the LAA wall via the anchor implanted through the inner endocardium layer, the middle myocardium layer, and the outer epicardium layer of the LAA wall.

2. The anchoring system of claim 1, further comprising:
   the LAA occluder device detachable from the anchor;
   the anchor configured to be left implanted through the LAA wall of the LAA at a first location;
   the LAA occluder device configured to be retrieved from the LAA;
   the LAA occluder device and a second anchor configured to be advanced into the LAA;
   the second anchor configured to be advanced through the LAA wall of the LAA at a second location;
   the LAA occluder device configured to expand to occlude the LAA; and
   the second anchor configured to pin the LAA occluder device against the LAA wall inside the LAA at the second location;
   wherein the LAA occluder device is configured to be moored to the LAA wall via the second anchor implanted through the inner endocardium layer, the middle myocardium layer, and the outer epicardium layer of the LAA wall.

3. The anchoring system of claim 1, further comprising:
   the LAA occluder device detachable from the anchor;
   the anchor configured to be left implanted through the LAA wall of the LAA;
   the LAA occluder device configured to be retrieved from the LAA;
   a second occluder device configured to be advanced into the LAA;
   the second LAA occluder device configured to be attached to the anchor implanted in the LAA wall of the LAA;
   the second LAA occluder device configured to expand to occlude the LAA; and
   the anchor configured to pin the second LAA occluder device against the LAA wall inside the LAA;
   wherein the second LAA occluder device is configured to be moored to the LAA wall via the anchor implanted through the inner endocardium layer, the middle myocardium layer, and the outer epicardium layer of the LAA wall.

4. The anchoring system of claim 1, wherein the anchor is separate from the occluder device.

5. The anchoring system of claim 4, further comprising:
a hole in the LAA occluder device; and
the shaft of the anchor configured to extend through the hole in the LAA occluder device.

6. The anchoring system of claim 1, wherein the anchor is self-expanding.

7. The anchoring system of claim 1, wherein the anchor comprises a sheave shape.

8. The anchoring system of claim 1, wherein the anchor comprises at least one coil.

9. The anchoring system of claim 8, wherein the first half of the anchor comprises a first coil and the second half of the anchor comprises a second coil, wherein the first coil is connected to the second coil via the shaft.

10. The anchoring system of claim 9, wherein the first coil unwinds in a first direction and the second coil unwinds in an opposite second direction.

11. The anchoring system of claim 1, wherein the anchor and the LAA occluder device are integral.

12. An anchoring system for implanting a left atrial appendage (LAA) occluder device within the LAA of a heart, comprising:
an anchor comprising a first half, an opposite second half and a shaft connecting the first half to the second half;
the first half of the anchor comprising the LAA occluder device configured to occlude the LAA of the heart to prevent blood from pooling, collecting and/or forming blood clots in the LAA during atrial fibrillation to reduce the risk of stroke;
a contracted first position of the anchor;
a deployed second position of the anchor;
the anchor configured to be advanced into the LAA, wherein the anchor is in the contracted first position;
the second half and the shaft of the anchor in the contracted first position configured to be advanced through a hole through an inner endocardium layer, a middle myocardium layer, and an outer epicardium layer of a LAA wall;
the second half of the anchor in the contracted first position configured to be advanced into a pericardial space from the LAA;
the second half of the anchor configured to expand from the contracted first position to the deployed second position in the pericardial space;
the shaft of the anchor configured to reside inside the hole through the inner endocardium layer, the middle myocardium layer, and the outer epicardium layer of the LAA wall;
the first half of the anchor comprising the LAA occluder device configured to expand from the contracted first position to the deployed second position to occlude the LAA;
the second half of the anchor configured to pin the LAA occluder device against the LAA wall inside the LAA in the deployed second position;
wherein the LAA occluder device is configured to be moored to the LAA wall via the second half of the anchor.

13. The anchoring system of claim 12, further comprising:
the anchor comprising the LAA occluder device configured to be retrieved from the LAA;
a second anchor configured to be advanced into the LAA;
a first half of the second anchor comprising a second LAA occluder device;
the second anchor configured to be implanted in the LAA wall of the LAA; and
the second LAA occluder device configured to be released to occlude the LAA;
a second half of the second anchor configured to pin the second LAA occluder device against the LAA wall inside the LAA;
wherein the second LAA occluder device is configured to be moored to the LAA wall via the second half of the second anchor.

14. The anchoring system of claim 12, wherein the anchor and the LAA occluder device are integral.

15. The anchoring system of claim 12, wherein the anchor and the LAA occluder device are self-expanding.

16. The anchoring system of claim 12, wherein the second half of the anchor comprises a sheave shape.

17. The anchoring system of claim 12, wherein the second half of the anchor comprises a coil.

* * * * *